(12) United States Patent
Rhodes

(10) Patent No.: US 8,515,551 B2
(45) Date of Patent: Aug. 20, 2013

(54) DIAGNOSTIC METHOD AND APPARATUS

(76) Inventor: Donald A. Rhodes, Corpus Christi, TX (US)

( * ) Notice: Subject to any disclaimer, the term of this patent is extended or adjusted under 35 U.S.C. 154(b) by 44 days.

(21) Appl. No.: 12/927,227

(22) Filed: Nov. 10, 2010

(65) Prior Publication Data

US 2011/0105916 A1     May 5, 2011

Related U.S. Application Data

(63) Continuation-in-part of application No. 11/374,903, filed on Mar. 14, 2006, now abandoned.

(51) Int. Cl.
*A61N 1/00* (2006.01)

(52) U.S. Cl.
USPC .......................................................... 607/67

(58) Field of Classification Search
USPC .................................. 600/301; 607/6, 67, 18
See application file for complete search history.

(56) References Cited

U.S. PATENT DOCUMENTS

| | | | | |
|---|---|---|---|---|
| 4,321,929 | A * | 3/1982 | Lemelson et al. | 600/301 |
| 5,661,538 | A * | 8/1997 | Carter | 351/237 |
| 6,826,429 | B2 * | 11/2004 | Johnson et al. | 607/67 |
| 2006/0100534 | A1 * | 5/2006 | Colombo et al. | 600/513 |

* cited by examiner

*Primary Examiner* — Christopher D Koharski
*Assistant Examiner* — Nadia Ahmad
(74) *Attorney, Agent, or Firm* — G. Turner Moller

(57) ABSTRACT

An electrical interferential device comprises a circuit for delivering electrical interferential energy into the body of a patient. A sensor detects a function of the autonomic nervous system of the patient and provides an output indicative of the response of the autonomic nervous system to the electrical interferential energy. A treatment regimen is selected which uses a combination of carrier and beat frequencies and electrode placement pattern that produce a desired response in the autonomic nervous system of the patient. In one embodiment of the invention, a diagnostic tool is used to determine which combination of carrier and beat frequencies are desirable and treatment is provided by a second electrical interferential device. In another embodiment of the invention, the same diagnostic tool or a portion of the same diagnostic tool may be used to treat the patient.

20 Claims, 1 Drawing Sheet

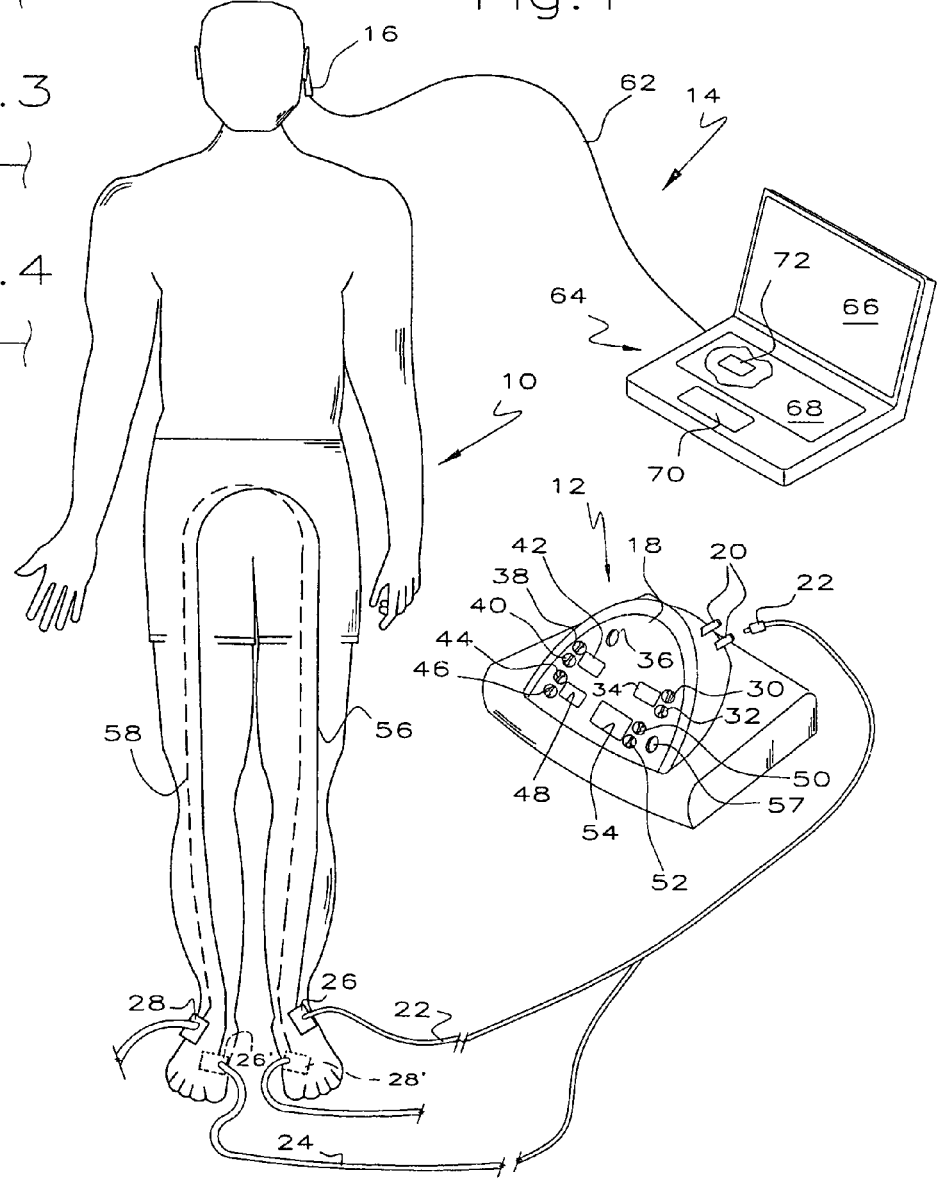

DIAGNOSTIC METHOD AND APPARATUS

This application is a continuation-in-part of application Ser. No. 11/374,903, filed Mar. 14, 2006 now abandoned.

This invention comprises a device and method for determining an optimum electrical or electromagnetic treatment.

BACKGROUND OF THE INVENTION

Electrical devices have been used in the prior art to treat pain or other symptoms by the application of energy in the form of alternating current electricity, direct current, magnetism and other forms of electromagnetic energy. As used herein, the adjective electrical, as in electrical energy, is intended to be generic to these different types of energy. One well accepted technique is known as electrical interferential therapy in which electrodes are connected in a crossing pattern adjacent the area to be treated. Alternating current is delivered through the electrodes into the body. One such device is commercially available from Dynatronics, Inc. of Salt Lake City, Utah. In the past, this type equipment has been used to treat small areas of the body because the electrodes are spaced relatively close together in the region to be treated. An electrical interferential device provides a carrier frequency and a second frequency that is only a few Hertz from the carrier frequency to produce a beat frequency which is the difference between the two. In most modern interference devices, the carrier frequency is fixed and the beat frequency can be adjusted slightly, e.g. over a range of 1-200 Hz, to provide different therapeutic results. In the past, these adjustments were made by the care provider in response to answers or reactions from the patient.

A promising interferential treatment is disclosed in U.S. Pat. No. 5,995,873, the disclosure of which is incorporated herein by reference. In this disclosure, two interferential devices are attached to a patient so the electrical signals travel along different nerve pathways to, around and away from the spinal column to treat pain and/or a variety of ailments, most of which involve some aspect of the sympathetic nervous system. The disclosure of this patent is extended in co-pending application Ser. No. 11/326,230, filed Jan. 5, 2006, the disclosure of which is also incorporated herein by reference.

Other disclosures of interest are found in U.S. Pat. Nos. 6,047,011; 6,126,183; 6,212,427 and 6,305,943.

SUMMARY OF THE INVENTION

It has been learned that substantial improvements in treating patients can be made by finding a desired parameter, or range of desired parameters, used in electrical treatments. Although a wide variety of electrical treatments can be optimized using the diagnostic method and apparatus of this invention, the currently most promising electrical treatment is known as electrical interferential treatment. In electrical interferential treatments, one may vary the carrier frequency, the beat frequency and/or the electrode pattern and then select a combination of frequencies and/or electrode pattern in response to a reaction of the autonomic nervous system of the patient. Thus, the patient is subjected to a single carrier frequency, a variety of beat frequencies and/or a variety of electrode patterns, or a variety of carrier frequencies, beat frequencies and electrode patterns. The response of the patient's autonomic nervous system is monitored in order to select a treatment regimen that appears most likely to be beneficial to the patient. Because of the difference in individuals and the difference in their ailments, the preferred treatment for one patient may vary significantly from the preferred treatment of the next patient.

In its broadest aspects, the approach of this invention is to deliver an electrical stimulus such as an electrical interferential treatment, i.e. a carrier and beat frequency, and monitor an aspect of the autonomic nervous system to determine the effect of a particular treatment on the patient. A series of tests using different parameters, including a variety of electrode patterns, of the particular treatment and monitoring an aspect of the autonomic nervous system to determine a preferred set of parameters for ultimate treatment of the patient. In the case of electrical interferential treatments, tests are run at different beat frequencies and/or at different carrier frequencies and/or at different electrode patterns to determine a test regimen that has the potential for substantial benefit to the patient. A combination of carrier and/or beat frequencies and electrode patterns is selected and thereafter used as an input to an electrical interferential device used by the patient in a series of treatments.

As discussed more fully hereinafter, a wide variety of techniques may be used to monitor the autonomic nervous system. For example, skin resistivity, peripheral skin temperature, pulse rate, heart rate variability, blood pressure, iris pupil diameter, respiration rate or other function of the autonomic nervous system may be monitored. Although these and other autonomic nervous system activities are suitable to monitor, a convenient technique is to monitor the heart rate variability with a device and software commercially available from Biocom Technologies of Poulsbo, Wash. known as HRV Live!.

It is accordingly an object of this invention to provide an improved diagnostic method and apparatus for selecting a preferred treatment regimen.

A more specific object of this invention is to provide an improved method and apparatus for determining which of a series of treatments has the potential for substantial beneficial results for the patient.

Another more specific object of this invention is to provide an improved diagnostic method and apparatus for determining a treatment which is specific to a particular patient.

These and other objects and advantages of this description will become more apparent as this description proceeds, reference being made to the accompanying drawings and appended claims.

BRIEF DESCRIPTION OF THE DRAWINGS

FIG. 1 is a combined schematic view of a diagnostic system of this invention and a pictorial view of the application of electrodes to a patient in accordance with this invention;

FIG. 2 is a partial schematic view of a skin resistivity monitor;

FIG. 3 is a partial schematic view of an iris pupil diameter measuring device; and FIG. 4 is a partial schematic view of a blood pressure monitor.

DETAILED DESCRIPTION

In the practice of this invention, electrical energy, in the form of electrical interferential pulses or other forms of therapy, are delivered into the patient's body. Any type of electrical or electromagnetic stimulation may be utilized to apply the treatment which is tested by the device of this invention. The particular type stimulation may include Transcutaneous Electrical Nerve Stimulation known as TENS, sympathetic therapy system, standard interferential units, direct current units and the like. All of these treatments cause changes in the autonomic nervous system, which is monitored by the testing unit of this invention. In other words, the effect of this electrical energy is monitored by one or more sensors that detect a function or an aspect of the autonomic nervous system. The sensed changes in the patient are then used to modify the configuration of the treatment machine and/or the placement of the electrodes used by the treatment machine. In other words, the results of the tests are used in an attempt to determine a preferred way to treat the patient by adjusting the treatment machine in response to the tests results obtained by this invention.

In the case of electrical interferential therapy, a series of trials are run on the patient, varying the carrier frequency, the beat frequency and/or the placement of the electrodes on the patient. The reaction of the autonomic nervous system of the patient is monitored. A determination is made of the combination of carrier frequency, beat frequency and electrode placement that produces a desired reaction of the patient which dictates or suggests a treatment regimen which has the potential to beneficially affect the patient. Further discussion of this invention will be in connection with electrical interferential treatment, it being understood that the invention is not so limited.

It is well known that the overall functioning of a living organism is controlled by the autonomic nervous system. It has two antagonistic branches—the sympathetic and parasympathetic nervous systems. Every organ is activated by one branch and inhibited by the other. Generally, when the organism is calm, organs such as the heart, lungs, and blood vessels are under parasympathetic control. When the organism is active, as during physical activity, psycho-emotional arousal or stress, these organs are dominated by the sympathetic nervous system. A healthy organism is capable of quickly adjusting to any external influence because of an adequate sympathetic response. Once that factor disappears, parasympathetic activity increases, which balances overall autonomic activity. It has become known that a large majority of people have overly active sympathetic nervous systems, i.e. their sympathetic nervous systems are overpowering or dominating their parasympathetic nervous system. This may have many effects, some of which may be controversial although many are not. In general, an overly active sympathetic nervous system tends to create or accentuate such diverse conditions or ailments such as diabetes type 1 and type 2, fibromyalgia, bipolar disorder, endometriosis, hypertension and other ailments such as disclosed in application Ser. No. 11/326,230, filed Jan. 5, 2006 or those ailments disclosed in U.S. Pat. No. 5,995,873.

A wide variety of techniques may be used to monitor the autonomic nervous system and thereby determine the effect of an interferential treatment on the patient. A preferred technique is to monitor heart rate variability. In the alternative, or in addition, to monitoring pulse rate, other manifestations of the autonomic nervous system may be monitored, for example, skin resistivity, peripheral skin temperature, pulse rate, blood pressure, iris pupil diameter, respiration rate, or any other indicator of autonomic nervous system function. A suitable skin resistivity sensor is known as MP System Electrodermal Response, available from Biopac Systems, Inc. of Goleta, Calif. A suitable peripheral skin temperature measuring sensor is known as Monotherm, available from Mallinckrot Medical of Hazelwood, Mo. A suitable blood pressure sensor is known as Omron wrist style blood pressure monitor, available from Omron Healthcare, Inc. of Bannockburn, Ill. A suitable iris pupil diameter sensor is known as NeurOptics pupillometer available from Neuroptics of Irvine, Calif. A suitable respiration rate sensor is known as Physiogard TM910, available from Mallinckroot Medical of Hazelwood, Mo.

Monitoring pulse rate is the preferred technique, to some extent because more experience has been achieved with pulse rate monitors, because commercially available devices and systems are available to monitor and analyze pulse rate and pulse rate changes and because pulse rate tends not to have mixed short and medium term effects which are often difficult to sort out. The analysis of pulse rate and pulse rate changes may be as simple or as sophisticated as desired. A simple technique is merely to obtain an average pulse rate after the patient has been subjected to electrical interferential energy for a time sufficient for the patient's autonomic nervous system to stabilize in response to the interferential energy. As will become more fully apparent hereinafter, one is looking for the conditions of interferential energy that produce a situation where the parasympathetic nervous system is more in balance with the sympathetic nervous system. In this simple analysis, one is looking for low pulse rates. As will become more fully apparent hereinafter, a much more sophisticated analysis is available using a device from Biocom Technologies of Poulsbo, Wash. known as an HRV Live! system.

Referring to FIG. 1, there is illustrated a patient 10 hooked up to a more-or-less conventional electrical interferential therapy device 12 such as is commercially available from Dynatronics, Inc. of Salt Lake City, Utah, to which reference is made for a more complete description thereof. The reaction of the patient 10 is monitored by a pulse rate monitor 14 having a conventional sensor 16 attached to the patient's ear lobe.

The electrical interferential therapy device 12 includes a housing 18 having one or more output receptacles 20 capable of accepting a jack 22 of insulated wire pairs 24 leading to electrode pairs 26, 26' and 28, 28'. Although the device 12 may have analog dials, it is preferably digitally controlled and provides a pair of buttons 30, 32 for increasing or decreasing the power or amplitude of the electrical energy delivered to the electrodes and is manipulated to deliver maximum energy consistent with patient comfort. A suitable display 34 provides an indication of the power output of the device 12. An electrode switch 36 is set to either two or four depending on whether one or two pair of electrodes are being used.

Standard commercially available electrical interference treatment devices have either a fixed carrier frequency or a minimally selective carrier frequency. For reasons which are mainly historical, these frequencies are conventionally 1850 Hz and 2850 Hz in the Sympathetic Therapy System from Dynatronics, Inc. and 4000 Hz in a device commercially available by Rehabilicare Corporation of St. Paul, Minn. Although this invention may be used in electrical interferential devices with fixed or commercially available frequencies, it is much preferred that the carrier frequency be adjustable in addition to the conventionally adjustable beat frequency.

To this end, the device 12 includes carrier frequency adjusting actuators 38, 40 and a carrier frequency display 42 and beat frequency actuators 44, 46 and a beat frequency display 48. The device 12 also includes a timer function having a pair of adjusting actuators 50, 52 and a timer display 54. The device 12 also includes an on-off switch 57.

The setting of the beat frequency selector switches 42, 44 is subject to some judgment. Experience has shown that the vast majority of desirable beat frequencies are between 4-104 beats per second (bps). In attempts to find the most desirable beat frequency in a reasonable time frame, this range has been subdivided into smaller segments. Experience has shown that some of the segments, at least at one carrier frequency where most efforts have been made, provide the most desirable beat frequency. The selector switches 44, 46, which may be analog or digital devices, control the "beat" frequency. For example, if the setting shown in the display 48 is ten, then the patient is subjected to ten beats per second. When it is desired to increase the beat frequency, the increase actuator 44 is depressed. When it is desired to decrease the beat frequency, the decrease actuator 46 is depressed. It will accordingly be seen that the device 12 includes a circuit for delivering therapeutic electrical energy into the body of the patient and more particularly includes a subcircuit for modifying the carrier frequency, the beat frequency and/or the amplitude of alternating current type energy.

The electrodes are attached to the patient's skin in a conventional manner, i.e. they are self adherent. The location of the electrodes on the patient establish the electrical circuit in the patient's body. As shown in FIG. 1, in one technique, one electrode 26 is placed adjacent the end or terminus of the right medial plantar nerve L5 and its matching electrode or mate 26' is placed adjacent the end or terminus of the left sural nerve S1, inferior to the left ankle bone (lateral malleolus) thereby establishing or creating a first circuit 58 in the patient's body. As used herein, the reference characters L5, S1 and the like are standard medical terminology for the nerve. Those skilled in the art will recognize L5 as being the nerve which extends away from the fifth lumbar vertebra and S1 as being the nerve which extends away from the first sacral vertebra.

Those skilled in the art will recognize that the terminus of the right medial plantar nerve L5 is located on the bottom of the right foot, approximately on the ball of the foot. The terminus of the left sural nerve S1 is located below the left ankle bone (lateral malleolus). Another electrode 28 is placed adjacent the terminus of the right sural nerve S1 and its matching electrode or mate 28' is placed adjacent the terminus of the left medial plantar nerve L5 thereby establishing a second circuit 60 in the patient's body. Turning the device 12 on delivers electrical energy through the circuits 56, 58. Experience has shown a decrease in pain in patients complaining of pain and a decrease in symptoms consistent with an imbalanced sympathetic nervous system. Those skilled in the art will recognize that the medial plantar nerves L5 and the sural nerves S1 terminate adjacent the spinal column near adjacent spinal vertebra, in the area of the connection to the lumbar sympathetic ganglia.

Other arrangements of the electrodes to stimulate other nerves are within the scope of this invention and are shown in U.S. Pat. No. 5,995,873. Initially, the patient is briefly subjected to no carrier frequency or frequencies or beat frequency or frequencies for a short period, typically about five minutes, in order to determine a baseline value of the pulse rate or other autonomic system function that is being monitored. Then, the patient is subjected to a series of tests, using different carrier frequencies, different beat frequencies and/or different electrode patterns in an attempt to determine an optimum or ideal combination of parameters that produce a desired effect on the autonomic nervous system and thereby determine a preferred treatment regimen. This may be accomplished in any suitable manner, as by holding two of the parameters constant and varying the third parameter until a sufficient number of tests have been done to give confidence in the results. For example, a series of first tests may be done with a fixed carrier frequency and fixed beat frequency in an attempt to determine an optimum electrode pattern followed by a series of second tests with what appears to be an optimum electrode pattern using fixed carrier frequencies and varying the beat frequency.

One of the most informative ways to evaluate the autonomic nervous system, including both branches, is heart rate variability analysis. This measures the time intervals between each two consecutive heartbeats, which vary under control of the autonomic nervous system. When the parasympathetic nervous system is dominant, the heart interbeat intervals oscillate at higher frequencies, typically in the range of 0.15-0.40 Hz. When the sympathetic nervous system is aroused, lower frequency oscillations take place.

A standard mathematical procedure exists for short term heart rate variability evaluation, suggested by the Task Force of the European Society of Cardiology and the North American Society of Pacing and Electrophysiology (1996). This provides both time and frequency domain analysis of the interbeat interval time series. There are three important parameters of frequency domain analysis within heart rate variability that reflect the levels of sympathetic and parasympathetic nervous system activity and their balance. The high frequency range of 0.15-0.40 Hz of the interbeat interval power spectrum, known as HF, reflects parasympathetic nervous system influence on heart rate. The low frequency range of 0.04-0.15 Hz of the interbeat interval power spectrum, known as LF, displays sympathetic nervous system influence. The LF/HF ratio is used to show the balance between the branches of the autonomic nervous system.

When initial studies were done on heart rate variability analysis, an electrocardiograph signal was used. The interbeat intervals were derived from the electrocardiograph as the intervals between consecutive R-peaks. This method is very accurate and reliable but has a serious disadvantage because it requires using complex electrocardiograph equipment and performing inconvenient multiple electrode placement. As the development of heart rate variability progressed and practitioners became comfortable with the correlation between an electrocardiograph measurement and a photoplethysmograph measurement from a finger or ear lobe clip optical sensor, the latter became widely accepted. A photoplethysmograph sensor emits an infrared light on the skin. The emitting light is partially absorbed by blood flow in the finger or ear lobe. The degree of light absorption and/or reflection is proportional to the changes in blood flow. The photoplethysmograph signal has periodic peaks representing blood vessel pulsation. This can also be used to derive the interbeat interval as the time between two photoplethysmograph peaks.

There are different evaluation methods for heart rate variability. Two methods recommended by the Task Force of the European Society of Cardiology are time domain methods and frequency domain methods. Although a great deal of information may be obtained from these methods, and a variety of approaches may be used to analyze the data, a preferred technique in this invention is to use frequency domain methods that determine LF/HF and normalized high frequency or NHF. As used in connection with the Biocom Technologies equipment, LF is defined as a band of power spectrum range between 0.04-0.15 Hz and reflects both sympathetic and parasympathetic activity. It will be apparent that this frequency range is an artifact of the Biocom Technologies device and other suitable frequency ranges are operable. In long term recordings, LF is a strong indicator of sympathetic activity. However, when the respiration rate is less than seven breaths per minute or during a deep breath, LF represents parasympathetic influence. Thus, when the patient is relaxed with slow and even breathing, LF values can be very high indicating increased parasympathetic activity rather than increase of sympathetic regulation. Thus, for the purpose of this invention, readings are taken when the patient is quiet, calm and relaxed.

High frequency power range or HF is a band of power spectrum range between 0.15-0.4 Hz. This measure reflects parasympathetic activity. Very low frequency or VLF is a band of power spectrum range between 0.0033-0.04 Hz. This measure is not well defined in terms of what physiological mechanism causes this power spectrum. It is generally known that this parameter indicates overall activity of various slow mechanisms of sympathetic function. Total power or TP is a short term estimate of the total power of power spectral density in the range of frequencies between 0-0.4 Hz. This parameter reflects overall autonomic activity where sympathetic activity is a primary contributor. Normalized high frequency NHF is the ratio of between the absolute value of HF and the difference between total power TP and very low frequency VLF.

In the diagnostic tests of this invention, one is seeking situations where the parasympathetic nervous system is enhanced compared to the sympathetic nervous system or the sympathetic nervous system is minimized in comparison to the parasympathetic nervous system. When using a sophisticated heart rate variability approach, this means that low values of LF, high values of HF, low values of the ratio of LF/HF, and high values of normalized high frequency NHF are being sought. The equipment of Biocom Technologies provides a report or printout showing the above values and others.

Referring to FIG. 1, the sensor 16 is of a conventional ear lobe clip optical sensor having an infrared light source directed onto the skin of the patient. Other alternatives to the pulse rate sensor 16 include a skin resistivity sensor 17 as shown in FIG. 2, an iris pupil diameter measuring device 19 as shown in FIG. 3 or a blood pressure monitor 21 as shown in FIG. 4. A series of signals are delivered from the sensor 16 through a suitable communication link 62, which is illustrated as a wire but which could easily be some form of wireless connection, to a computer 64 which is typically a conventional laptop computer having a display or screen 66, a keyboard 68 and some type mouse 70. The computer 64 is equipped with suitable memory and/or storage 72, which may be referred to as a recorder. It will accordingly be seen that the computer 64 provides a calculating device for manipulating the sensor outputs and providing a data processor output representative of the reaction of the patient to the electrical interferential energy as shown in Tables I and II.

After determining a baseline value of heart rate and heart rate variability, the patient is subjected to a series of tests using one or more carrier frequencies and one or more beat frequencies and one or more electrode placement patterns such as shown in FIGS. 1-5 of U.S. Pat. No. 5,995,873. The results of the Biocom Technologies analysis is obtained, an example of which is shown in Table I, as taken from a 59 year old Hispanic male using simultaneous carrier frequencies of 1850 Hz and 2850 Hz, a fixed beat frequency of 8-12 and a series of electrode placement patterns. These frequencies are the standard carrier frequencies of the Sympathetic Therapy System of Dynatronics, Inc.

TABLE I

| electrode pattern | Total Power | VLF | LF | HF | LF/HF | Normalized LF | Normalized HF |
|---|---|---|---|---|---|---|---|
| 43i | 27949 | 6095 | 14749 | 7104 | 2.1 | 67.5 | 32.5 |
| 43d | 6324 | 2240 | 2118 | 1966 | 1.1 | 51.9 | 48.1 |
| 43c | 12299 | 2078 | 7605 | 2616 | 2.9 | 74.4 | 25.6 |

TABLE I-continued

| electrode pattern | Total Power | VLF | LF | HF | LF/HF | Normalized LF | Normalized HF |
|---|---|---|---|---|---|---|---|
| 43b | 518 | 203 | 168 | 147 | 1.1 | 53.3 | 46.7 |
| 43a | 1171 | 243 | 644 | 283 | 2.3 | 69.5 | 30.5 |

These particular electrode patterns comprise four pairs of magnetic electrodes similar to that shown in U.S. Pat. No. 6,453,204 that for convenience are color coded red, white, yellow and black on the Sympathetic Therapy System from Dynatronics, Inc. Non-magnetic electrodes of this type are provided by Dynatronics, Inc. and the magnets are added by Alan Neuromedical Technologies, 6001 South Staples, Suite 1-B, Corpus Christi, Tex. 78414. These magnets are generally flat with a North pole on one side and a South pole on the opposite side. Magnetic electrodes on the right side of the body are with the South pole facing toward the patient and on top of the electrode which touches the patient. Magnetic electrodes on the left side of the body are with the North pole facing toward the patient and on top of the electrode which touches the patient. In the following descriptions of the electrode patterns, the abbreviations R1, R2, W1, W2, Y1, Y2, B1 and B2 are used for individual red, white, yellow and black electrodes.

Electrode Pattern 43i

R1 is high on the upper inside of the left thigh. R2 is on the sole of the right foot, midway between the big toe and heel, adjacent the edge. W1 is high on the upper inside of the right thigh. W2 is on the bottom of the left foot, in the center, at the front of the heel. Y1 is on the outside of the right foot, directly below (half on and half off) the ankle bone. Y2 is on the inside of the left foot on the soft spot in front of the ankle when the foot is flexed. B1 is on the bottom of the left foot, near the ball of the foot, immediately rearward of the big toe. B2 is on the inside of the right foot, on the soft spot in front of the ankle when the foot is flexed.

Electrode Pattern 43d

R1 is on the top of the left foot, immediately rearward of the gap between the big toe and the next adjacent toe. R2 is on the outside of the right foot, directly below (half on and half off) the ankle bone. W1 is on the outside of the left foot, directly below (half on and half off) the ankle bone. W2 is on the top of the right foot, immediately rearward of the gap between the big toe and the next adjacent toe. Y1 is on the left side of the left shin, two inches below the kneecap, at the top of the bone. One should feel the muscle move when the left foot is flexed and twisted. Y2 is on the back of the right knee, in the center of the leg. B1 is on the right side of the right shin, two inches below the kneecap, at the top of the bone. One should feel the muscle move when the left foot is flexed and twisted. B2 is on the back of the left knee, in the center of the leg.

Electrode Pattern 43c

R1 is on the bottom of the left foot, on the ball, immediately rearward of the big toe. R2 is on the outside of the right foot, directly below (half on and half off) the ankle bone. W1 is on the bottom of the right foot, on the ball, immediately rearward of the big toe. W2 is on the outside of the left foot, directly below (half on and half off) the ankle bone. Y1 is on the bottom of the left foot, in the center, immediately forward of the heel. Y2 is on inside of the right foot, on the soft spot in front of the ankle when the foot is flexed. B1 is on the bottom of the right foot, in the center, immediately forward of the heel. B2 is on the inside of the left foot, on the soft spot in front of the ankle when the foot is flexed.

Electrode Pattern 43b

Y1 is on the bottom of the left foot, on the ball, immediately rearward of the big toe. Y2 is on the inside of the right foot, on the soft spot in front of the ankle bone when the foot is flexed. B1 is on the bottom of the right foot, in the center, forwardly of the heel. B2 is on the inside of the left foot, on the soft spot in front of the ankle bone when the foot is flexed. R1 is on the outside of the right foot, directly below (half on and half off) the ankle bone. R2 is on the inside of the left foot, almost touching B2, on a line toward the base of the nail of the big toe. W1 is on the outside of the left foot, directly below (half on and half off) the ankle bone. W2 is on the inside of the right foot, almost touching Y2, on a line toward the base of the nail of the big toe.

Electrode Pattern 43a

Y1 is on the bottom of the left foot, in the center, forward of the heel. Y2 is on the inside of the right foot, on the soft spot in front of the ankle bone when the foot is flexed. B1 is on the bottom of the right foot, on the ball, immediately rearward of the big toe. B2 is on the inside of the left foot, on the soft spot in front of the ankle bone when the foot is flexed. R1 is on the outside of the right foot, directly below (half on and half off) the ankle bone. R2 is on the inside of the left foot, almost touching B2, on a line toward the base of the nail of the big toe. W1 is on the outside of the left foot, directly below (half on and half off) the ankle bone. W2 is on the inside of the right foot, almost touching Y2, on a line toward the base of the nail of the big toe.

Those skilled in the art will recognize the placement of the electrodes to be adjacent the terminus of nerve endings in the extremities and similar to, but not identical, to the electrode placement patterns in U.S. Pat. No. 5,995,873. It will be apparent that many different electrode patterns are possible.

An analysis of Table I shows that the occurrence of a low LF/HF ratio and a high value of NHF occurs at a carrier frequency of 1850 and 2850 Hz, a beat frequency of 8-12 and electrode pattern 43b. This combination of carrier and beat frequencies and electrode placement pattern is then used as an input to an interferential treatment device, similar to the device 12, used by the patient in a series of treatments, either in a care provider's office or in the patient's home. Any treatment device in the custody of the patient may be set with the desired frequencies in such a manner that the patient cannot vary them or the treatment device may simply be a clone of the device 12. Any treatments may be daily, twice daily, or any other suitable interval. Examples of the results of the diagnostic method and apparatus of this invention is shown in the following case studies.

A second example of testing done on a 66 year old Caucasian male is found in Table II, using carrier frequencies of 1850 and 2850 Hz and a series of beat frequency ranges as shown and a fixed electrode placement pattern 149b on the patient's upper extremities. The column entitled "beat frequency" shows a range of beat frequencies. Standard interferential treatment machines, such as made by Dynatronics, Inc., produce beat frequencies which vary slightly in order to prevent the nerves to which the electrodes 26, 28 deliver electrical energy from becoming acclimated to the beats. This adjustment may be random or may be in a pattern that is provided in the commercial devices.

TABLE II

| beat frequency | Total Power | VLF | LF | HF | LF/HF | Normalized LF | Normalized HF |
|---|---|---|---|---|---|---|---|
| 2-6 | 46.8 | 10.1 | 9.6 | 27.1 | 0.4 | 26.2 | 73.8 |
| 8-12 | 28.3 | 3.1 | 2.4 | 22.7 | 0.1 | 9.6 | 90.4 |
| 12-18 | 31.2 | 7.5 | 1.7 | 21.9 | 0.1 | 7.1 | 92.9 |
| 26-44 | 36.8 | 6.6 | 2.7 | 27.5 | 0.1 | 9.1 | 90.9 |
| 45-85 | 58.4 | 19.7 | 6.8 | 31.9 | 0.2 | 17.5 | 82.5 |
| 86-104 | 41.6 | 6.5 | 3.6 | 31.6 | 0.1 | 10.3 | 89.7 |

The placement pattern 149b includes magnetic electrodes for R1, R2, W1 and W2 "with O" on the right side of the body and "without O" on the left side. Electrodes B1, B2, Y1 and Y2 are unmagnetized electrodes. R1 is on the back of the left arm in the center, midway between the elbow and shoulder. R2 is on the outside of the right hand, in the thick fleshly area between the thumb and index finger. B1 is on the inside of the right palm below the base of the index finger, on the knuckle. B2 is on the inside of the left thumb pad towards the tip. Y1 is on the inside of the left palm below the base of the index finger, on the knuckle. Y2 is the inside of the right thumb pad towards the tip. W1 is on the back of the right arm in the center, midway between the elbow and shoulder. W2 is on the outside of the left hand, in the thick fleshly area between the thumb and index finger.

An analysis of Table I shows the low value of the LF/HF ratio is common and not much different than the high value. The highest value of NHF does not vary tremendously from the low value but the highest value is 92.9, so carrier frequencies of 1850 and 2850 are selected along with a beat frequency of 12-18 beats per second. This combination of carrier and beat frequencies is then used as an input to an interferential treatment device, similar to the device 12, used by the patient in a series of treatments, either in a care provider's office or in the patient's home. Any treatment device in the custody of the patient may be set with the desired frequencies in such a manner that the patient cannot vary them or the treatment device may simply be a clone of the device 12. Any treatments may be daily, twice daily, or any other suitable interval. Examples of the results of the diagnostic method and apparatus of this invention is shown in the following case studies. A comparison of Tables I and II shows that sometimes there is a wide difference between a patient's response to different beat frequencies or electrode placement and sometimes there is not a great deal of difference.

Case study 1

A sixty seven year old Caucasian man was diagnosed as having pancreatic cancer. The patient had severe nausea, which had not responded to any of the traditional medications. In addition, he had been suffering from severe abdominal pain. The unit 12 was utilized to set the beat frequency of the interferential treatments using carrier frequencies of 1850 and 2850 as provided by the Sympathetic Therapy System from Dynatronics, Inc. It was found, utilizing this testing, that the beat frequency of 2 to 6 beats per second was most effective in augmenting the effects of the parasympathetic nervous system and decreasing the effects of the sympathetic nervous system. The patient began receiving twice per day treatments of two simultaneous interferential treatments from the right hand to the left hand and from the right foot to the left foot. Within two weeks, the nausea had virtually disappeared. In addition, the abdominal pain was markedly reduced. At the end of three weeks, the beat frequency was checked again. It was found that now the beat frequency of 12 to 18 beats per second was the most effective in augmenting the effects of the parasympathetic nervous system and decreasing the effects of the sympathetic nervous system.

Case Study 2

A forty seven year old Caucasian woman had suffered from Rheumatoid arthritis for most of her life. She had been treated with all of the usual oral medications for this disease and had multiple surgeries. However, she still was in significant pain and could barely walk, despite the significant amount of Prednisone that she was taking. The device 12 was utilized to set the beat frequency of the interferential treatments using carrier frequencies of 1850 and 2850 provided by the Sympathetic Therapy System from Dynatronics, Inc. It was found, utilizing this testing, that the beat frequency of 96 to 102 beats per second was most effective in augmenting the effects of the parasympathetic nervous system and decreasing the effects of the sympathetic nervous system. The patient began receiving twice per day treatments of two simultaneous interferential treatments from the right hand to the left hand and from the right foot to the left foot. Within one week, the patient was able to walk with only minimal pain. Within one month, the patient was able to walk without pain. The Prednisone was slowly withdrawn and, within three months, the patient was able to walk pain-free without pain or medication.

Case Study 3

A sixty four year old Hispanic man had been diagnosed as having diabetes type 2 for 25 years and had been treated for hypertension more than 20 years. Before starting treatment, the patient was taking 80 units of insulin and an oral medication for hypertension. The device 12 was utilized to set the beat frequency of the interferential treatments using carrier frequencies of 1850 and 2850 as provided by the Sympathetic Therapy System from Dynatronics, Inc. It was found, utilizing this testing, that the beat frequency of 2 to 6 beats per second was most effective in augmenting the effects of the parasympathetic nervous system and decreasing the effects of the sympathetic nervous system. The patient began receiving twice per day treatments of two simultaneous interferential treatments from the right hand to the left hand and from the right foot to the left foot. Within one month, the patient's blood pressure began normalizing and his fasting blood sugars began to lower toward normal. Within two months, the patient's blood pressure had decreased to the point that he was able to discontinue the oral medication. In addition, the patient's blood sugars had decreased to the point that his usage of insulin was decreased. Within three months, the patient no longer required insulin and yet his blood sugars were normal. The patient's blood pressure continued to be normal even though he was no longer taking oral medication.

Case Study 4

A fourteen-year-old Caucasian girl was diagnosed as having Complex Regional Pain Syndrome (CRPS) in her right leg and foot. Prior to beginning treatments she had "terrible pain" in her right foot and leg and was unable to bear any weight on her right foot and leg. The device 12 was utilized to set the beat frequency of the interferential treatments using carrier frequencies of 1850 and 2850 as provided by the Sympathetic Therapy System from Dynatronics, Inc. It was found, utilizing this testing, that the beat frequency of 26 to 34 beats per second was most effective in augmenting the effects of the parasympathetic nervous system and decreasing the effects of the sympathetic nervous system. The patient was unable to tolerate any electrodes on her right foot or leg. Therefore, the patient began receiving twice per day treatments of two simultaneous interferential treatments from the right hand to the left hand and from the left foot to the left hand. Within one week of treatments, the pain was decreasing in the patient's right foot and leg. The patient was then able to tolerate twice per day treatments of two simultaneous interferential treatments from the right hand to the left hand and from the right foot to the left foot. After one month of treatments, the patient was able to walk pain-free, without crutches. Two weeks later, the patient again began having symptoms in her right foot and leg. When the device 12 was utilized to set the beat frequency of the interferential treatments. It was found, utilizing this testing, that the beat frequency of 2 to 6 beats per second was now the most effective in augmenting the effects of the parasympathetic nervous system and decreasing the effects of the sympathetic nervous system. Within several days after changing the beat frequency, the patient was again symptom-free.

Case Study 5

A seventeen year and one half year old Caucasian boy was diagnosed with Duchenne Muscular Dystrophy. When first seen, the boy was able to walk only with difficulty. At the onset of treatment, the patient was receiving 51 milligrams of a steroid known as Deflazacort per day. The patient was treated by interferential guided by a computer assessment of autonomic nervous function as disclosed herein. Electrodes were attached to the patient's hands and feet and interferential frequencies applied. Various techniques were used to determine the response of the autonomic nervous system to the applied frequencies and appropriate adjustments were made in the location of the electrodes and the applied frequencies. About fifteen weeks later after twice daily treatments, the patient had improved significantly as evidenced by his improved ability to walk. The dosage of Deflazacort was reduced to 48 milligrams daily.

It is not yet known whether this treatment will prolong the life of the patient. It is unarguable that he is in better physical condition with less pronounced symptoms of Duchenne muscular dystrophy than when first seen. In addition, his condition continued to improve over a time period exceeding fifteen months. This is a sufficient time for the disease to progress to an extent where the physical ability of any patient with Duchenne muscular dystrophy noticeably deteriorates. This improvement has continued in spite of the continued decrease in steroids. The dosage was reduced to 37 milligrams of Deflazacort daily which is a 25% reduction from the original dose of 51 milligrams. Despite the reduction in steroids, the patient grew stronger rather than weaker. The patient improved to the extent that he could walk and use his arms to pick up items that were impossible to pick up for the five preceding years. Duchenne muscular dystrophy is a progressive ailment and, so far as is known, no other treatment has been successful in reversing symptoms of Duchenne muscular dystrophy, particularly with reduced levels of steroid medication.

Case Study 6

A 3½ year old boy was diagnosed with Duchenne muscular dystrophy. Electrical interferential treatments were begun using the technique disclosed to optimize the placement of electrodes and the beat frequency. Eighteen months after the beginning of treatments, the patient appeared normal and acted normal. The patient could run fast enough the see his hair blow. In a young boy afflicted with Duchenne muscular dystrophy eighteen months after diagnosis, one would expect the patient to have considerably reduced ability to walk and jump. In contrast, this patient could jump and walk substantially better than he could when first seen. Thus, the symptoms of Duchenne muscular dystrophy were reversed to a considerable extent in this patient. An initial MRI showed pathological fatty intrusion into the muscles of the legs and buttocks which is a tell tale indication of Duchenne muscular dystrophy. One year later, a follow up MRI showed no pathological fatty intrusion into these muscles. The latter MRI indicates that no only has the muscle destruction stopped but the pathological fatty intrusion was replaced by normal muscle.

In addition, at 5½ years old, this patient was able to ski three mornings in a row and run up the hillside each afternoon to ride a toboggan down the hill. He takes karate, rides a bike and has normal balance. In other words, he acted like a normal boy of his age. Prior to this treatment, he could not walk across a room without falling down as if he were drunk. Prior to this treatment, his calf muscles were contracted and enlarged, known as pseudohypertrophy which is also a classic indication of Duchenne muscular muscular dystrophy. With this treatment, the calf muscles have become of normal size and are as supple as normal calf muscle would be for a child of his age.

Although this invention has been disclosed and described in its preferred forms with a certain degree of particularity, it is understood that the present disclosure of the preferred forms is only by way of example and that numerous changes in the details of operation and in the combination and arrangement of parts may be resorted to without departing from the spirit and scope of the invention as hereinafter claimed.

I claim:

1. A diagnostic system for identifying a preferred treatment for a patient comprising at least two pairs of electrodes; each of said pairs adapted to be temporarily attached to opposite limbs of a patient, respectively, at various selected locations and an electrical circuit connected to the electrodes for producing treatments comprising conducting a plurality of carrier frequencies and a plurality of beat frequencies through said electrodes for delivering therapeutic electrical interferential energy to the patient at said selected locations; said treatments producing a variety of responses of the autonomic nervous system wherein sympathetic and parasympathetic activity occurs in response to said treatments; a sensor for monitoring the autonomic nervous system of the patient for detecting said sympathetic and parasympathetic nervous system activity and providing a series of outputs indicative of said activity; and a recorder for recording the outputs whereby the electrodes may be repositioned and the carrier frequency can be changed and the beat frequency can be changed to produce a series of said treatments, at least some of which produce indications of autonomic nervous system activity that promotes augmenting the activity of the parasympathetic nervous system and decreasing the effects of the activity of the sympathetic nervous system thereby identifying an effective set of treatments to be applied to a patient.

2. The diagnostic system of claim 1 wherein the sensor is a heart rate sensor.

3. The diagnostic system of claim 1 wherein the sensor is a blood pressure monitor.

4. The diagnostic system of claim 1 wherein the sensor is a skin resistivity sensor.

5. The diagnostic system of claim 1 wherein the sensor is an iris pupil diameter measuring device.

6. The diagnostic system of claim 1 wherein the recorder comprises a data processor having a calculating device for manipulating the sensor outputs and providing a data processor output representative of the reaction of the patient to the electrical interferential energy.

7. The diagnostic system of claim 1 wherein the recorder comprises a data processor having a calculating device for manipulating the sensor outputs and providing a data processor output representative of sympathetic nervous system activity and parasympathetic nervous system activity.

8. The diagnostic system of claim 1 wherein the recorder comprises a data processor having a calculating device for manipulating the sensor outputs and providing a data processor output representing a ratio of sympathetic nervous system activity and parasympathetic nervous system activity.

9. The diagnostic system of claim 1 wherein the circuit includes a subcircuit for adjusting the carrier frequency and the system determines which combination of carrier and beat frequencies that produce a desired reaction of the autonomic nervous system.

10. The diagnostic system of claim 1 wherein the system comprises a data processor having a calculating device for manipulating the sensor outputs and providing a data processor output representative of sympathetic nervous system activity and parasympathetic nervous system activity.

11. The diagnostic system of claim 1 wherein the sensor is a peripheral skin thermometer.

12. A method of determining a preferred treatment regimen for a patient, comprising
conducting a series of treatments comprising applying a first set of electrodes to opposite limbs of the patient, respectively, at selected first locations and applying another set of electrodes to opposite limbs of the patient, respectively, at selected second locations, applying different therapeutic treatments to the patient comprising conducting at least one carrier frequency and at least one beat frequency to said electrodes for delivering therapeutic electrical interferential energy to the patient at said selected locations, said treatments producing a variety of responses of the autonomic nervous system wherein sympathetic and parasympathetic activity occurs in response to said treatments, and sensing a parameter related to autonomic nervous system activity of the patient in response to each of said treatments;
and selecting at least one of the therapeutic treatments that promotes augmenting the activity of the parasympathetic nervous system and decreasing the effects of the activity of the sympathetic nervous system of the patient, whereby a series of the at least one selected therapeutic treatment can be applied to the patient.

13. The method of claim 12 wherein the sensing steps comprise sensing heart rate variability.

14. The method of claim 12 wherein the sensing steps comprise sensing blood pressure.

15. The method of claim 12 wherein the step of sensing comprises sensing skin resistivity.

16. The method of claim 12 wherein the step of sensing comprises sensing iris pupil diameter.

17. The method of claim 12 wherein the step of sensing comprises sensing peripheral skin temperature.

18. The method of claim 12 wherein the conducting step comprises moving the electrodes to opposite limbs of the patient at third and fourth locations and repeating the steps of applying different therapeutic treatments to the patient.

19. The method of claim 12 wherein the sensing step comprises sensing a parameter providing a proxy for blood flow from the group consisting essentially of heart rate, blood pressure, skin resistivity and peripheral skin temperature.

20. The diagnostic system of claim 1 further comprising a display device for displaying the outputs thereby allowing an operator to select between treatments to be delivered to a patient.

* * * * *